US006372196B1

(12) United States Patent
Santar et al.

(10) Patent No.: US 6,372,196 B1
(45) Date of Patent: Apr. 16, 2002

(54) HEMOSTATICALLY ACTIVE AEROSOL COMPOSITION OF POLYANHYDROGLUCORONIC ACIDS AND ITS SALTS

(75) Inventors: Ivan Santar, Predklasteri; Frantisek Kiss, Brno; Jiri Briestensky, Cernilov, all of (CS)

(73) Assignee: Alpenstock Holdings Limited, Dublin (IE)

( * ) Notice: Subject to any disclaimer, the term of this patent is extended or adjusted under 35 U.S.C. 154(b) by 0 days.

(21) Appl. No.: 09/359,381

(22) Filed: Jul. 23, 1999

(30) Foreign Application Priority Data

Jan. 30, 1997 (IE) ..................................... 970062

(51) Int. Cl.[7] ..................................... A61K 9/12
(52) U.S. Cl. ..................................... 424/45; 424/46
(58) Field of Search ..................................... 424/45, 46

(56) References Cited

FOREIGN PATENT DOCUMENTS

GB 1254534 11/1971

OTHER PUBLICATIONS

Chemical Abstracts, vol. 117, No.1, Kaspar, "Microembolzation Agent", XP002062982, Jan. 4, 1993.
Chemical Abstracts, vol. 106, No. 26, Blazicek et al, "Hemo–Static Substance", XP002062983, Jun. 29, 1987.

Chemical Abstracts, vol. 121, No. 1, Stelmah et al, "Polycapran Evaluation of Hemostatic Action", XP002062984, Jan. 2, 1995.

Patent Abstracts of Japan, vol. 8, No. 236, JP 59 116213 A (Unitika KK), Oct. 30, 1984.

*Primary Examiner*—Raj Bawa
(74) *Attorney, Agent, or Firm*—Jacobson Holman, PLLC

(57) ABSTRACT

Wounds involving minor lesions such as cuts, excoriations, burns, scalds and various kinds of open efflorescence require rapid covering to arrest bleeding, to disinfect the wound area and to suppress secondary microbial contamination. The present invention is a hemostatically active aerosol composition comprised of microdispersed polyanhydroglucuronic acid and salts thereof and from 0.75 to 0.995 parts by weight of a dispergating/propellant system. The system includes compounds which are nonpolar or of low polarity with a surface tension of less than 30 mN/M and a permitivity of 10 kilohertz of less than 10 and at least one compound selected from the group consisting of a fluorinated or perfluorinated alkane, a $C_3$ to $C_8$ cycloalkane and a fluorinated or perfluorinated aliphatic ether. Such an invention provides a product for use as a sterile absorbable local hemostatic for both the layman and the professional public, enabling easy and rapid application in common wounds with minimal detriment to the environment.

51 Claims, No Drawings

HEMOSTATICALLY ACTIVE AEROSOL COMPOSITION OF POLYANHYDROGLUCORONIC ACIDS AND ITS SALTS

BACKGROUND OF THE INVENTION

The invention relates to a composition of polyanhydroglucuronic acid (PAGA) and its salts. The term polyanhydroglucuronic acid and salts thereof as used herein includes copolymers thereof, especially with anhydroglucose.

INTRODUCTION

1. Field of the Invention

Wounds occurring in human and veterinary practice often involve minor lesions such as cuts, excoriations, bums, scalds, and various kinds of open efflorescences be it of eczematous or bacterial origin. Such lesions require rapid covering to arrest bleeding, to disinfect the wound area, and to suppress secondary microbial contamination.

It is widely accepted that the healing essentially consists of three stages which may be simply defined, as: inflammatory/exsudative phase (Phase 1), proliferative phase (Phase 2), differentiation phase (Phase 3).

It is especially important for the healing process to arrest bleeding and to suppress secondary microbial contamination of the wound. Through infiltration of the, exsudate, the wound is supplied with leucocytes, neutrophilic granulocytes and monocytes, subsequently being converted to macrophages. Insufficient treatment of even minor lesions may thus give way to massive infections and to considerable complications of the healing process.

2. Description of the Related Art

The hemostatic effect of oxidised cellulose, introduced into health care practice by pioneering work of Kenyon, Nevell, Rogovin, Jasnitzky and others, has been known since the 1940's. Mechanisms underlying the hemostatic activity of PAGA have been recently explicitly reported e.g. by V A Stelmah et al. (Vestn. Beloruss. Gos. Univ., Ser. 2 (1993), (2) 43–5; cf. CA 1994:570118) to consist in an acceleration of formation of thrombi. The oxidised cellulose is prevailingly manufactured in the form of woven or knitted tissue (such as Surgicel or Interceed by Johnson & Johnson, USA). Its application is therefore mostly limited to specialised institutions such as surgical clinics or ambulances. Also, the existing products have certain contraindications due to their relatively high acidic character. Another disadvantage of the existing products is due to the fact that opening of the sterile packaging outside a sterile area may bring about bacterial contamination of both the sterile product and the wound; the same problem of course applies even to powder form packaged and sterilised in e.g. plastic bottles.

A detailed discussion regarding polyanhydroglucuronic acid and salts thereof is included in our co-pending Patent Application having the same date of filing as this application.

Pressurised aerosol packagings have been available from the 1930's, originally as insect sprays also used during World War II, using chlorofluoroalkanes as the propellant gas. They have been applied to pharmaceutical products since the 1950's, and there has been considerable development towards other types of propellants—less depleting the ozone layer and less contributing to global warming—in the last decades. However, there is no awareness of an aerosol packaged hemostatic of the polyanhydroglucuronic acid type prepared on the basis of oxidised cellulose as yet.

It is therefore the aim of the present invention to provide a product based on polyanhydroglucuronic acid and its salts for use as a sterile absorbable local hemostatic for mass usage by both layman and professional public, enabling easy and rapid application in common wounds and lesions and minimising detrimental effects on the environment.

BRIEF SUMMARY OF THE INVENTION

According to the invention, there is provided a hemostatically active aerosol composition comprising from 0.005 to 0.25 weight parts of microdispersed/microdispersable polyanhydroglucuronic acid and/or salts thereof and from 0.75 to 0.995 weight parts of a suitable dispergating/propellant system wherein the dispergating/propellant system includes liquids which are non-polar or of low polarity and have a surface tension of less than 30 mN/M and a permitivity at 10 kilohertz of less than 10. The term polyanhydroglucuronic acid and salts thereof includes copolymers thereof, especially with anhydroglucose.

The hemostatically active aerosol composition of the invention enables easy and rapid administration and ensures permanent readiness for use, sterility at repeated application, and increased stability due to exclusion of air and UV light access to the product in a pressurised aerosol packaging.

The composition may include at least one pharmaceutical adjuvant which may be selected from one or more substances having suitable anti-microbial, anti-viral, antimycotic and/or anti-parasitic effects.

In one embodiment of the invention, the stable microdispersed polyanhydroglucuronic acid and/or salts thereof have the form of particles of 0.1 to 80 $\mu$m preferably 5 to 15 $\mu$m, in size.

In one embodiment of the invention, the propellant used comprises aliphatic and/or alicyclic hydrocarbons with a number of carbon atoms from 1 to 6 and/or aliphatic ethers and/or fluorinated and/or perfluorinated aliphatic hydrocarbons and/or ethers, and/or carbon dioxide and/or nitrogen and/or rare gases and, as the case may be, other auxiliary substances.

The polyanhydroglucuronic acid salts are preferably selected from calcium, magnesium, sodium and/or potassium salts.

The polyanhydroglucuronic acid and/or salts thereof are preferably prepared by a method wherein a polyanhydroglucuronic acid-containing material is subjected to partial or complete hydrolysis and neutralisation in an oxidative environment, the hydrolysate undergoing fractional coagulation to form a stable microdispersed product.

This method provides stable polyanhydroglucuronic acid and salts thereof in essentially a single process carried out in a single vessel.

Preferably the hydrolysis is carried out in an aqueous solution of inorganic and/or organic salts and/or bases. Most preferably the inorganic and/or organic salts and/or bases used for hydrolysis are chlorides, sulphates, carbonates, formates, or acetates of alkali and/or alkaline earth metals, hydroxides of alkali and/or alkaline earth metals, alkylamines, or alkanolamines, in concentrations ranging from 1 to $10^{-3}$ to 5 mol/l.

In an especially preferred embodiment of the invention the oxidative environment during hydrolysis is established by the presence of agents selected from one or more of hydrogen, sodium or magnesium peroxide, peroxacides and their salts, hypochlorites and chlorites.

Preferably the procedure is carried out at a pH of from 1 to 12, and preferably, at a temperature of from 0 to 100° C.

In a preferred embodiment of the invention the polyanhydroglucuronic acid-containing material is obtained by oxidation of a suitable polysaccharide, such as native or regenerated cellulose or starch.

The polyanhydroglucuronic acid and salts thereof preferably contain in their polymeric chain from 8 to 30 percent by weight of carboxyl groups, at least 80 percent by weight of these groups being of the uronic type, at most 5 per cent by weight of carbonyl groups, and at most 0.5 percent by weight of bound nitrogen.

Preferably the product contains at most 0.2 percent by weight of bound nitrogen in the polymeric chain.

In a preferred embodiment of the invention the molecular mass of the polymeric chain is from $1\times10^3$ to $3\times10^3$) Daltons most preferably from $5\times10^3$ to $1.5\times10^3$ Daltons.

The content of the carboxyl groups is in the range of from 12 to 26 percent by weight and at least 95 percent of these groups are of the uronic type.

In a particularly preferred embodiment of the invention the product contains at most 1 percent by weight of carbonyl groups. Typically the carbonyl groups are intra- and intermolecular 2,6 and 3,6 hemiacetals, 2,4-hemialdals and C2–C3 aldehydes.

Because neutralisation and refining is carried out in a single operation the process is cost effective.

As the product is in a microdispersed form there is enhanced sorption and greater accessibility for blood. Therefore the biological availability is increased and a rapid onset of hemostatis. We have also observed that the product also assists wound healing as a large surface area is presented which is quickly penetrated by body fluids and goes into solution in these fluids. We believe that the product then chemically degrades to achieve more rapid absorption and enhancement of the wound healing process.

The overall homogeneity of the distribution of oxidised groups within the product is increased. Thus, the product has improved reactivity and accessibility to reactive sites for the purpose of binding ocher substances such as pharmacologically acnve substances to the product. The average degree of polymerisation is decreased, the distribution of the polymerisation is narrowed and the amount of cellulosic fractions are reduced. This also assists in biodegradation.

The polyanhydroglucuronic acid and salts thereof may be made up of particles sized from 0.1 to 100 $\mu$m and/or fibres of from 5 to 30 $\mu$m diameter and up to 30 mm length.

Preferably the hydrolysate is let to undergo fractional coagulation by a suitable water-miscible organic solvent, the coagulated product is washed, or dehydrated, using a suitable water-miscible organic solvent, and/or converted, in an appropriate manner, for intended subsequent use.

Preferably the inorganic and/or organic salts and/or bases preferably used for hydrolysis are chlorides, sulphates, carbonates, formates, or acetates or alkali and/or alkaline earth metals, hydroxides of alkali and/or alkaline earth metals, alkylamines, or alkanolamines, in concentrations ranging from $1\times10^{-3}$ to 5 mol/l.

Preferably the oxidative environment during hydrolysis is established by the presence of oxidative agents such as hydrogen, sodium or magnesium peroxide, peroxacides and their salts, hypochlorites, or chlorites.

DETAILED DESCRIPTION OF THE INVENTION

The invention will be more clearly understood from the following description thereof given by way of example only.

The essence of the invention consists in the ability of the microdispersed polyanhydroglucuronic acid and salts thereof to form stable dispersions in physiologically indifferent liquids displaying low to zero rate of sedimentation low viscosity of these colloid-dispersion non-aqueous systems and no tendency to agglomerate at concentrations of 0.5 to 15% b/w.

Of important advantage is the fact that the physicochemical properties of the microdispersed polyanhydroglucuronic acid can be controlled to fit the dispergating liquid or mixture of liquids, thus allowing stable systems suitable as spray fillings to be prepared.

Extensive tests have shown that the microdispersed polyanhydroglucuronic acid and salts thereof prepared by controlled hydrolysis and fractionation, mostly in the form of particles smaller than the size of an erythrocyte, is capable of stimulating the activity of histiocytes and macrophages, which represents another essential advantage of the application of such substances. At the same time, they effectively arrest capillary bleeding of the wound area while getting incorporated into the fibrin net formed. Due to small size of the order of microns, the particles of the microdispersed polyanhydroglucuronic acid and salts thereof undergo, dependent on the chemical composition and physiochemical properties, relatively rapid enzymatic hydrolysis in the wound environment yielding glucose and glucuronic acid, substances inherent to living organism, as final products; in fact, histological observations indicate that they are presumably incorporated into body mucopolysaccharides. Close to neutral pH value of extracts of salts of microdispersed polyanhydroglucuronic acid also substantially contributes to their biocompatibility; no adverse secondary effects due to acidic nature have been reported in their applications.

The presence of reactive carboxyl groups in the microdispersed polyanhydroglucuronic acid and salts thereof is the basis for their ability to chemically bind substances with antibacterial effects such as e.g. derivatives of biguanid, quaternary ammonium salts, or aminosaccharide based antibiotics. Bactericidal activity is also observed for salts or complex salts of certain cations, such as $Zn^{2-}$, $Cu^{2-}$, and to a limited extent $Ag^{+}$, with microdispersed polyanhydroglucuronic acid.

Similarly, we have observed that preparations based on the microdispersed polyanhydroglucuronic acid and salts thereof display certain insecticidal activity, This activity can be enhanced using hydrophobic reactivity of polyanhydroglucuronic acid molecules which allows to anchor on the powder substance non-toxic synthetic derivatives of natural pyrethrins such as pyrethroids, notably Permethrin (cis/trans isomer ratio 1:3). Another advantage of compositions according to the invention is thus represented by the possibility to combine in a single product, hemostatic, bacteriostatic, and insecticidal function. This is important in veterinary medicine for the treatment of both traumatic and artificial lesions in e.g. sheep and cattle, in that it provides a temporary protection against microbial infection and insect attack during healing.

An example of successful combination of an antibiotic and a hemostatic may be represented by the application of neomycine ut sulfas and bacitracinum zincicum of bound to a sodium/calcium salt of microdispersed polyanhydroglucuronic acid.

The main problem that had to be solved within the invention concerns the choice of dispergating liquids and propellants to be used in aerosol packaging formulations of the microdispersed polyanhydroglucuronic acid and salts thereof.

Extensive tests have surprisingly revealed that the use of organosols containing several different substituents or highly polar substituents caused the system to easily form coacervates or even to coagulate.

We have found that eg alcoholic dispersions display a relatively low stability with a rapid coagulation and/or sedimentation of particles. The stability is increased with increasing size of the aliphatic chain of the molecule but the application of higher alcohols is limited from the physiological point of view. We have also found that the hemostatic efficacy of the microdispersed polyanhydroglucuronic acid based products in the initial phase immediately after the spray administration is reduced by the presence of water or polyhydroxycompounds such as glycerol and its derivatives, glycols and polyglycols. Univalent alcohols such as ethanol can induce a stinging pain on application to the wound. Substances of the latter types are therefore preferably avoided in the formulation.

Coagulation and/or sedimentation was surprisingly equally observed in systems where a substance with low polarity has been used, but the molecule contained several different substituents giving rise to an electrostatic non-equilibrium, the examples of these being dichlorotetrafluoroethane or trichlorofluoromethane. In contrast low polar substances such as alkanes, C1 to C8 cycloalkanes, or their fluorinated and perfluorinated derivatives, yielded stable dispersion systems with a low sedimentation rate. Examples are methane, ethane, propane, butane, isobutane, pentane, 2-methylbutane, 2-methylpropane, 2,2-dimethylpropane and the like. Substances with 3 to 5 carbon atoms such as pentane, neopentane, or a pure petrol fraction free from mercaptanes and aromatics may preferably be used to reduce loss at administration, to improve fixation of the substance upon the treated area.

We have further found that the organic liquid molecule may also contain a heteroatom, preferably oxygen, in the main chain without deteriorating the system stability. Such substances would involve ethers such as dimethylether, diethylether, but also perfluorinated ethers of the methoxy- or ethoxy-nonafluorobutane type.

Extensive tests have shown that the product, though involving an important number of hydrophilic polar groups, can best be dispergated in low polar or non-polar liquids with a low surface tension and low relative permitivity. In contrast, we have found that liquids with higher polarity and higher surface tension tend to support agglomeration of the product particles and thus to jeopardies the correct function of the aerosol packaging. Besides the effect of microparticles with a large specific surface area the good dispersability of the microdispersed polyanhydroglucuronic acid and salts thereof may be attributed to their ability to enter, in spite of the presence of hydrophilic groups, hydrophobic interactions with the dispergating liquids. The results indicate that stable dispersion systems can preferably be obtained using those of the above substances which display a value of the relative permitivity (dielectric constant at 25° C. and 10 kHz) less than 10, preferably less than 5, and that of the surface tension less than 30 mN/m, preferably less than 18 mN/m. Thus the substances recommended for use involve, preferably, C3 to C5 alkanes, isoalkanes, or cycloalkanes, 1,1,1,2-tetrafluoroethane, dimethylether, methoxy- and ethoxy-nonafluorobutane and mixtures thereof.

Besides the ability to form low sedimenting dispersion systems, the overall criteria limiting the choice of suitable dispergator/propellant systems further include: physiological indifference (low toxicity, zero or minimum skin and cardiac sensitisation at exposures up to 100000 ppm, no mutagenicity and carcinogenicity, minimum solubility in water and body fluids), indifference in contact with the active substance, high volatility and low heat of evaporation, ability to fix the active substance in the first phase immediately after application on the wound surface, environmental acceptability, and cost.

It is difficult to draw a sharp demarcation line between the dispergating medium suitable for the microdispersed polyanhydroglucuronic acid and salts thereof and the propellant since in some cases both functions can be provided for by one and the same substance such as e.g. n-butane or isobutane. In general, the relevant substances may especially involve:

a) Aliphatic and alicyclic hydrocarbons with 1 to 6 carbon atoms, or aliphatic ethers, notably dimethylether, diethylether, and diisopropylether. While aliphatic hydrocarbons with 1 to 3 carbon atoms could well serve as dispergators for the microdispersed polyanhydroglucuronic acid and salts thereof when under pressure, they evaporate immediately at the output of the spray outlet and thus increase the powder dissipation on spraying and insufficiently fix the powder on the wound surface. It is therefore preferable to use higher hydrocarbons such as n-butane, isobutane, n-pentane, or isopentane for the given purpose. This group may also include petrolether, pentane/isopentane fraction from petroleum distillation, or a mixture of liquid hydrocarbons currently distributed under the name of medicinal petrol, under the obvious condition of being pure enough from aromatic hydrocarbons and mercaptanes. From the ether group, dimethylether can preferably be used with respect to its suitable physicochemical characteristics.

b) Nonflammable compounds known as fluorohydrocarbons (HFC), perfluorocarbons (PFC), and recently introduced hydrofluoroethers (HFE). Compared to chlorofluorocarbons (CFC), the HFC's, PFC's and HFE's display much reduced life time in the atmosphere and zero to very low ozone-depleting potential (ODP) and global warming potential (GWP). Some may have a slightly increased toxicity and bioreactivity; however, their contact with the wound is very short due to the rapid evaporation rate. The most suitable choice with respect to the properties may be represented by 1,1,1,2-tetrafluoroethane (HFC 134a) or hydrofluoro-ethers such as methoxy-nonafluoroethane (HFE 7100) or 1,1,1,2,3,3-hexafluoro-3-methoxypropane, all of these substances being acceptable from both the physiological and environmental point of view.

Representatives of both above groups are liquids or substances liquefiable at low pressures (0.2–1.4 Mpa) at normal conditions. Further alternatives include:

c) Gaseous substances, which cannot be liquefied at normal conditions, but capable of being absorbed, at least partially in the powder active substance or in the liquid dispersion system. These include notably carbon dioxide and nitrous oxide.

d) Gaseous substances not liquefiable at normal conditions and displaying a very limited absorption ability in the liquid dispersion system, such as rare gases, air and nitrogen.

All of these substances can further be suitably combined with each other to provide for an optimized function of the spray. Based on extensive testing, the preferred combinations include systems such as n-butane or n-pentane/$CO_2$, medicinal petrol/HFC 134a, isopentane/dimethylether, medicinal petrol/HFE 7100/HFC134a, HFE 7100/$CO_2$, n-pentane/HFE 7100/$N_2$.

In summary, the important fact underlying the present invention is that the polyanhydroglucuronic acid and salts thereof create stable dispersion concentrates in liquids that do not compromise the environment, displaying zero or low values of both the ODP and GWP potentials.

An important advantage of the aerosol packaged hemostatic according to the invention consists in the fact that the contents of the packaging can repeatedly be used without the loss of their sterility. The dosing of the active substance can accurately be directed to the wound surface where the powder gets well anchored due to the relatively high speed of incidence of an indifferent dispersion in a liquid that is immiscible with the body fluids and evaporates within a few seconds.

Certain adverse secondary effects are reported for the above listed dispergating and propellant substances, such as weak narcotic effects or skin degreasing on contact for C5 hydrocarbons. However, no such effects have been observed during extensive application tests of the sprays according to the invention because of small applied amounts and short contact time.

An additional specific advantage can be attained when using substances listed under a) above or combinations of substances listed under a) and c) above for preparing the stable dispersions of the microdispersed polyanhydroglucuronic acid and salts thereof. Such formulations of the spray allow a simple terminal sterilisation of the finished aerosol packagings to be preformed by gamma radiation.

EXAMPLES

Example 1

In this example, the raw material for preparing a salt of microdispersed polyanhydroglucuronic acid were cotton linters containing 99.1% b/w (by weight) of α-cellulose and oxidised in 60% nitric acid with an admixture of 3.6% nitrous acid at a temperature of 28° C. in analogy with the procedure of GBP 709684. The resulting product contained:

| | |
|---|---|
| carboxyl groups | 13.7% b/w |
| carbonyl groups | 4.2% b/w |
| bound nitrogen | 0.48% b/w |

In a 3000 ml laboratory mixer, 1000 ml of water and 0.158 g of calcium acetate were heated up to 60° C. and stirred at 600 rpm. After dissolution of calcium acetate, 2 , of the above defined oxidised cotton linters containing about 8% of volatile matter were added, temperature increased to 98° C., and the mixture stirred at 2800 rpm for 15 minutes while maintaining the temperature. The temperature was then decreased back to 60° C. pH adjusted to 8.5 by adding sodium hydroxide solution, 25 g of 30% hydrogen peroxide were added, and the hydrolysis continued at the reduced temperature for another 15 minutes. Subsequently the reaction system was cooled down to 40° C., stirring reduced to 300 rpm. and 1500 ml of 92% ethanol were added stepwise during about 10 minutes. The resulting colloid dispersion solution was then filtered, the residue was dispergated into 50% water-ethanol mixture and allowed to stand for one hour. After another filtration the residue was redispergated into 100 ml of isopropanol and allowed to stand for 6 hours. The same procedure was repeated once more, and then the product was filtered and dried in a vacuum drier at a temperature of 40° C.

An analysis of the product obtained yielded:

| | |
|---|---|
| loss on drying | 1.25% b/w |
| carboxyl group content | 16.8% b/w |
| carbonyl groups | 0.5% b/w |
| bound nitrogen content | 0.13% b/w |
| calcium content | 2.1% b/w |
| sodium content | 5.2% b/w |
| particle size | 2 to 5 μm |
| specific surface area | 98 $m^2/g$ |
| Molecular weight | 6 × $10^4$ Daltons |

The product can be used directly as a hemostatic powder or as a component of an aerosol powder spray.

Example 2

A hemostatic composition in pressurised aerosol packaging has been prepared using stable microdispersed polyanhydroglucuronic acid in the form of calcium/sodium salt as described in Example 1 above. The equipment used included a stainless steel 1000 liter mixer with a propeller stirrer, a stainless steel 30 liter/min metering pump with inner circulation and an aerosol filling machine (Pamasol type) with one filling head for the dispersion concentrate and two filling heads for the propellant.

The bulk substance used in this example was a calcium/sodium salt of microdispersed polyanhydroglucuronic acid having the following characteristics:

| | |
|---|---|
| particle size 20–60 μm | 2% b/w |
| 10–20 μm | 32% b/w |
| ≦10 μm | 66% b/w |
| specific surface area | 105 $m^2/g$ |
| carboxyl group content (total) | 20.2% b/w |
| carboxyl group content (uronic) | 18.2% b/w |
| free formaldehyde | 0% b/w |
| foreign particles | 0% b/w |
| calcium content | 3.9% b/w |
| sodium content | 5.6% b/w |
| bound nitrogen content | 0.02% b/w |

Chlorohexidine hydrochloride (Ferrosan) in concentration of 0.1% b/w was added as a bacteriostatic adjuvant. The dispergation/ propellant system involved a liquid hydrocarbon mixture (known as medicinal petrol) with density of 652 $kg/m^3$ boiling point 55° C., and residue after evaporation <2 ppm and 1,1,1,2-tetrafluoroethane (HFC 134a).

40 kg of the active substance was placed into the mixer. 150 liters of the liquid hydrocarbon mixture added, and the system stirred at 600 rpm for 5 minutes. After addition of 1 kg of chlorohexidine hydrochloride and of another 250 liters of the liquid hydrocarbon mixture, the system was further stirred until a uniform dispersion was obtained. The metering pump was used to dose the dispersion via the filling head of the filling machine into aerosol cans of 80 ml nominal volume in doses of 31 g per can. After inserting a suitable valve, another filling head was used to add 18 g per can of the 1,1,1,2-tetrafluoroethane propellant.

The finished spray can be used for treatment of bleeding wounds by both the professional or a layman.

Example 3

The same equipment was used as in Example 2. The active substance consisted of two components, MDOC1 with the same characteristics as in Example 2, and MDOC2 involving a zinc/calcium/sodium salt of microdispersed polyanhydroglucuronic acid having the following properties:

| | |
|---|---|
| carboxyl group content | 19.5% b/w |
| free formaldehyde | 0% b/w |
| zinc content | 9.5% b/w |
| calcium content | 3.9% b/w |
| sodium content | 5.6% b/w |
| bound nitrogen content | 0% b/w |

Neomycinum ut sulfas and Bacitracinum zincicum were used as antibacterial adjuvants, n-pentane having density of 625 kg/$m^3$, and boiling point 36° C., as the dispergator, and carbon dioxide (edible grade quality) as the propellant.

38.8 kg of MDOC1 and 1.2 kg of MDOC2 was placed into the mixer together with 0.132 kg, of Neomycinum ut sulfas and 0.143 kg (10 IU) of Bacitracinum zincicum, 200 liters of n-pentane added, and the system thoroughly stirred. Another 200 liters of n-pentane were then added and stirred for another 10 minutes. Aerosol cans of 80 ml nominal volume were then filled in doses of 31 per can, and, after inserting the valves another filling head was used to pressurise the can by addition of 2 g or compressed carbon dioxide.

The finished spray can be used for professional treatment of bleeding wounds and lesions.

Example 4

A thoroughly homogenised uniform powder mixture of microdispersed polyanhydroglucuronic acid in the form of magnesium/calcium/sodium and zinc/calcium/sodium salts in the mass ratio of 32:1 is filled into aerosol cans of to 210 ml nominal volume in doses of 8 g per can on a powder dosing machine (Bosch). Upon closing the can with an appropriate valve, the can is pressurised on the aerosol filling machine by adding 20 g of n-butane and 30 g of dimethylether. Finished and gamma sterilised sprays then can be used for treatment of smaller bums or scalds. It can also be applied in e.g. urological or gynecological surgery.

Example 5

Into the mixer as described in Example 2, 25 kg of calcium/sodium salt of microdispersed polyanhydroglucuronic acid (Example 1), 5.0 kg of calcium stearate, 0.4 kg of chlorohexidine hydrochloride, and 7.7 kg of Permethrin with cis/trans ratio of 25:75 (ICI Plant Protection) are successively placed. After addition of 400 liters of n-pentane and 99 kg of methoxy-nonafluorobutane (HFE 7100), the contents of the mixer are stirred for 15 minutes. The uniform dispersion is then filled into aerosol cans of 210 ml nominal volume in doses of 110 g per can on the filling machine and closed with an appropriate valve. Another filling head is then used to add 50 g per can of dimethylether.

The finished spray is designed for use in veterinary practice for treatment of wounds and lesions in e.g. sheep and cattle, simultaneously providing a temporary protection against microbial and/or insect attack.

Example 6

A hydrophilised adduct (MDOC-ACV) of 9-[(2-hydroxy-methoxy)-methyl]-guanin (acyclovir) and a calcium/sodium salt of microdispersed polyanhydroglucuronic acid as described in Example 1, the content of acyclovir in the MDOC-ACV adduct being 50.5% b/w.

A homogenised mixture of the adduct, the magnesium/calcium/sodium salt of microdispersed polyanhydroglucuronic acid according to Example 1, and the zinc/calcium/sodium salt thereof according to Example 2 in the mass ratio of 8.7:0.3:1.0 is filled into aerosol cans of 120 ml nominal volume in doses of 4 g per can on a powder dosing machine (Bosch). Upon closing the can with an appropriate valve, the aerosol filling machine is used to pressurise the can by adding 25 g of 2,2-dimethylpropane (neopentane) with a density of 625 kg/$m^3$. and boiling point 9.6° C., on filling head 1, and 23 g of dimethylether with a density of 668 kg/$m^3$.

The finished spray is packed and sterilised by gamma radiation with a dose of 25 kGy and used as a dusting powder in the treatment of e.g. herpes zoster, enabling an easy application and good efficacy even in hairy areas of the body.

The invention is not limited to the embodiments hereinbefore described which may be varied in detail.

What is claimed is:

1. A hemostatically active anhydrous aerosol composition comprising from 0.005 to 0.25 parts by weight of microdispersed polyanhydroglucuronic acid and acceptable salts thereof and from 0.75 to 0.995 parts by weight of a suitable dispergating/propellant system, wherein the dispergating/propellant system is non-polar or of low polarity, has a surface tension of less than 300 mN/M, and a permitivity at 10 kilohertz of less than 10, and wherein the dispergating/propellant system is selected from the group consisting of alkanes, fluorinated alkanes, perfluorinated alkanes, $C_3$ to $C_8$ cycloalkanes, fluorinated $C_3$ to $C_8$ cycloalkanes, perfluorinated $C_3$ to $C_8$ cycloalkanes, aliphatic ethers, fluorinated aliphatic ethers, and perfluorinated aliphatic ethers.

2. The aerosol composition as claimed in claim 1 wherein the surface tension is less than 18 mN/M.

3. The aerosol composition as claimed in claim 1 wherein the permitivity at 10 kilohertz is less than 5.

4. The aerosol composition as claimed in claim 1 wherein the dispergating/propellant system does not include water or polyhydroxy compounds.

5. The aerosol composition as claimed in claim 1 wherein the dispergating/propellant system does not include a univalent alcohol.

6. The aerosol composition as claimed in claim 1 wherein the dispergating/propellant system is selected from the group consisting of methane, ethane, propane, butane, isobutane, pentane, 2-methylbutane, 2-methylpropane, and 2,2-dimethylpropane.

7. The aerosol composition as claimed in claim 6 wherein the dispergating/propellant system is a petrol fraction free from mercaptans and aromatics or is selected from the group consisting of $C_3$ to $C_5$ alkanes, fluorinated $C_3$ to $C_5$, perfluorinated $C_3$ to $C_5$, $C_3$ to $C_5$ cycloalkanes, fluorinated $C_3$ to $C_5$ cycloalkanes, and perfluorinated $C_3$ to $C_5$ cycloalkanes.

8. The aerosol composition as claimed in claim 1 wherein the dispergating/propellant system includes a heteroatom in the main chain.

9. The aerosol composition as claimed in claim 8 wherein the heteroatom is oxygen.

10. The aerosol composition as claimed in claim 1 wherein the system is selected from the group consisting of dimethylether, diethylether, and perfluorinated ethers, methoxy- or ethoxy-nonflurobutane.

11. The aerosol composition as claimed in claim 1 wherein the system is selected from the group consisting of $C_3$ to $C_4$ alkanes, isoalkanes, or cycloalkanes, 1,1,1,2-tetrafluroethane, dimethylether, methoxy- and ethoxy-nonfluorobutane.

12. The aerosol composition as claimed in claim 1 wherein the system is selected from the group consisting of alkanes, cycloalkanes, aliphatic ether or mixtures thereof.

13. The aerosol composition as claimed in claim 12 wherein the alkanes are selected from the group consisting of 4 to 6 carbon atoms.

14. The aerosol composition a claimed in claim 12 wherein the aliphatic ethers are selected from dimethylether, diethylether and diisopropylether.

15. The aerosol composition as claimed in claim 14 wherein the aliphatic ether is dimethylether.

16. The aerosol composition as claimed in claim 1 wherein the system is selected from the group consisting of hydrofluorocarbons, perfluorocarbons or hydrofluroethers.

17. The aerosol composition as claimed in claim 16 wherein the system includes one or more hydrofluorocarbons or hydrofluoroethers.

18. The aerosol composition as claimed in claim 17 wherein the hydrofluorocarbon is 1,1,1,2-tetrafluoroethane (HFC 134a).

19. The aerosol composition as claimed in claim 17 wherein the hydrofluoroethers are selected from the group consisting of methoxy nonafluoroethane and 1,1,1,2,3,3,-hexa fluoro-3-methoxypropane.

20. The aerosol composition as claimed in claim 1 further comprising a gaseous substance which is absorbable by the microdispersed polyanhydroglucuronic acid and salts thereof.

21. The aerosol composition as claimed in claim 20 wherein the gaseous substance is selected from the group consisting of carbons dioxide and nitrous oxide.

22. The aerosol composition as claimed in claim 20 wherein the gaseous substance has limited absorbability in the disperagating/propellant system.

23. The aerosol composition as claimed in claim 22 wherein the gaseous substance is selected from the group consisting of rare gases, air and nitrogen.

24. The aerosol composition as claimed in claim 1 wherein the disperagating/propellant system includes n-butane and carbon dioxide.

25. The aerosol composition as claimed in claim 1 wherein the disperagating/propellant system includes n-pentane and carbon dioxide.

26. The aerosol composition as claimed in claim 1 wherein the disperagating/propellant system includes a purified de-aromatised distillate of petroleum and 1,1,1,2-tetrafluoroethane.

27. The aerosol composition as claimed in claim 1 wherein the disperagating/propellant system includes isopentane and dimethylether.

28. The aerosol composition as claimed in claim 1 wherein the disperagating/propellant system includes a purified de-aromatised distillate of petroleum, methoxy nonafluoroethane and 1,1,1,2-tetrafluoroethane.

29. The aerosol composition as claimed in claim 1 wherein the disperagating/propellant system includes methoxy nonafluoroethane and $CO_2$.

30. The aerosol composition as claimed in claim 1 wherein the disperagating/propellant system includes n-pentane, methoxy nonafluoroethane and $N_2$.

31. The aerosol composition as claimed in claim 1 wherein the composition includes at least one pharmaceutically acceptable adjuvant.

32. The aerosol composition as claimed in claim 31 wherein the adjuvant is selected from the group consisting of anti-microbial substances, anti-viral substances, anti-mycotic substances, and anti-parasitic substances.

33. The aerosol composition as claimed in claim 1 wherein the stable microdispersed polyanhydroglucuronic acid and salts thereof are particles having a size from 0.1 to 80 $\mu$m.

34. The aerosol composition as claimed in claim 33 wherein the stable microdispersed polyanhydroglucuronic acid and salts thereof are in the form of particles having a size of from 5 to 15 $\mu$m.

35. The aerosol composition as claimed in claim 1 wherein the polyanhydroglucuronic salts are selected from the group consisting of calcium, magnesium, sodium and potassium salts.

36. The aerosol composition as claimed in claim 1 wherein the microdispersed polyanhydroglucuronic acid and salts thereof contain in their polymeric chain from 8 to 30 percent by weight of carboxyl groups, at least 80 percent by weight of these groups being uronic acids, at most 5 per cent by weight of carbonyl groups, and at most 0.5 percent by weight of bound nitrogen.

37. The aerosol composition as claimed in claim 36 wherein the polyanhydroglucuronic acid and salts thereof contain in their polymeric chain at most 0.2 percent by weight of bound nitrogen.

38. The aerosol composition as claimed in claim 36 wherein the polyanhydroglucuronic acid and salts thereof have a molecular mass of the polymeric chain of from $1\times10^3$ to $3\times10^5$ Daltons.

39. The aerosol composition as claimed in claim 36 wherein the polyanhydroglucuronic acid and salts thereof have a molecular mass of the polymeric chain of from $5\times10^3$ to $1.5\times10^5$ Daltons.

40. The aerosol composition as claimed in claim 36 wherein the content of carboxyl groups is in the range of from 12 to 26 percent by weight, at least 95 percent of these groups being uronic acids.

41. The aerosol composition as claimed in claim 36 wherein the polymeric chain contains at most 1 percent by weight of carbonyl groups.

42. The aerosol composition as claimed in claim 36 wherein the carbonyl groups are intra- and intermolecular 2,6 and 3,6 hemiacetals, 2,4-hemialdals and C2–C3 aldehydes.

43. The aerosol composition as claimed in claim 1 wherein the polyanhydroglucuronic acid and salts thereof are prepared by a method wherein a material comprising polyanhydroglucuronic acid is hydrolyzed and neutralized in an oxidative environment to give a hydrolysate which undergoes fractional coagulation to form a microdispersed product.

44. The aerosol composition as claimed in claim 43 wherein the polyanhydroglucuronic acid is hydrolyzed in an aqueous solution of inorganic salts, organic salts, inorganic bases, organic bases, or a combination thereof.

45. The aerosol composition as claimed in claim 44 wherein the inorganic salts, organic salts, inorganic bases, and organic bases are selected from the group consisting of: chlorides, sulphates, carbonates, formates, or acetates of alkali or alkaline earth metals; hydroxides of alkali or alkaline earth metals; alkylamines; and alkanolamines, in concentrations ranging from 1 to $10^{-3}$ to 5 mol/l.

46. The aerosol composition as claimed in claim 43 wherein the oxidative environment is established by the presence of agents selected from the group consisting of: one or more of hydrogen; sodium or magnesium peroxide; sodium or magnesium peroxacides; sodium or magnesium salts; hypochlorites; and chlorites.

47. The composition as claimed in claim 43 wherein the hydrolysate undergoes fractional coagulation by a suitable water-miscible organic solvent.

48. The composition as claimed in claim 47 wherein the microdispersed product is washed or dehydrated with a suitable water-miscible organic solvent.

49. The composition as claimed in claim 43 wherein the method is carried out at a pH of 1 to 12.

50. The composition as claimed in claim 43 wherein the method is carried out at a temperature of 0 to 100° C.

51. The composition as claimed in claim 43 wherein the material is obtained by oxidation of a suitable polysaccharide, including native, regenerated cellulose or starch.

* * * * *